United States Patent [19]
Kim et al.

[11] Patent Number: 5,507,189
[45] Date of Patent: Apr. 16, 1996

[54] APPARATUS FOR EVALUATING PLANE STRAIN STRETCH FORMABILITY, AND METHOD THEREFOR

[75] Inventors: Young S. Kim; Jeong C. Kim; Won J. Choi; Rae W. Chang; Ki S. Kim; Moon H. Yu, all of Pohang, Rep. of Korea

[73] Assignees: Pohang Iron & Steel Co., Ltd.; Research Institute of Industrial Science & Technology, Kyong Sang Book, Rep. of Korea

[21] Appl. No.: 295,655

[22] PCT Filed: Dec. 29, 1993

[86] PCT No.: PCT/KR93/00124

§ 371 Date: Aug. 25, 1994

§ 102(e) Date: Aug. 25, 1994

[87] PCT Pub. No.: WO94/16307

PCT Pub. Date: Jul. 21, 1994

[30] Foreign Application Priority Data

Dec. 30, 1992 [KR] Rep. of Korea .................. 1992-26474

[51] Int. Cl.[6] ..................................................... G01N 19/00
[52] U.S. Cl. .................................................. 73/838; 73/834
[58] Field of Search ........................... 73/830, 831, 835, 73/834, 845, 851, 838–839

[56] References Cited

U.S. PATENT DOCUMENTS

| | | | |
|---|---|---|---|
| 2,645,937 | 7/1953 | Kalmusky et al. | 73/838 |
| 3,319,462 | 5/1967 | Ostrowski | 73/835 |
| 4,099,408 | 7/1978 | Ludwigson | 73/834 |

FOREIGN PATENT DOCUMENTS

184004 7/1966 U.S.S.R. .................. 73/838

*Primary Examiner*—Richard E. Chilcot, Jr.
*Assistant Examiner*—Max H. Noori
*Attorney, Agent, or Firm*—Webb Ziesenheim Bruening Logsdon Orkin & Hanson

[57] ABSTRACT

Apparatus and a method for evaluating the plane strain stretch formability for thin steel sheets used in automotive bodies to provide easy evaluation of the plane strain stretch formability. The apparatus includes: a lower die and an upper die with a lock bead installed thereon. A rectangularly shaped test specimen is inserted between the upper and lower dies and, and is clamped by means of the lock bead along the circumferential edge of the test specimen, so that the material of the test specimen can be moved into the upper die. A punch is elevated to apply a stretch forming force on the test specimen, and then, the plane strain stretch formability is evaluated based on the fracture limit punch height at the instant of the fracture. The punch has a saddle-like, semi-cylindrical shape.

10 Claims, 8 Drawing Sheets

APPARATUS FOR EVALUATING PLANE STRAIN STRETCH FORMABILITY, AND METHOD THEREFOR

FIELD OF THE INVENTION

The present invention relates to an apparatus and a method for evaluating the stamping formability for thin steel sheets used in manufacturing automotive bodies. In particular, the present invention relates to an apparatus and a method for evaluating the stretch formability which refers to the fracture limit under the plane strain mode which occupies the greater part of the fractures occurring during the stamping process for the automotive steel sheets.

BACKGROUND OF THE INVENTION

Figure 1:
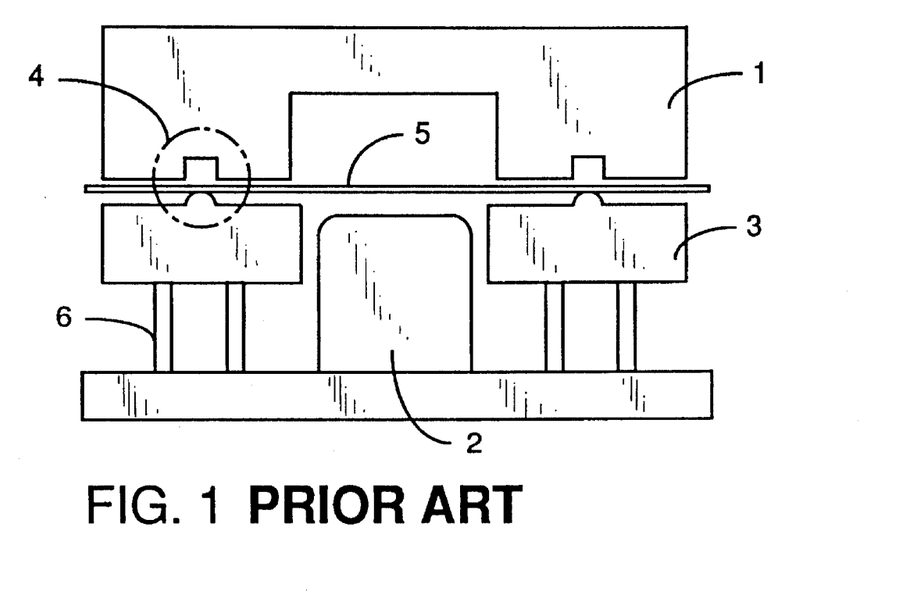
FIG. 1 is a sectional view of the usual stamping die.
Figure 2:
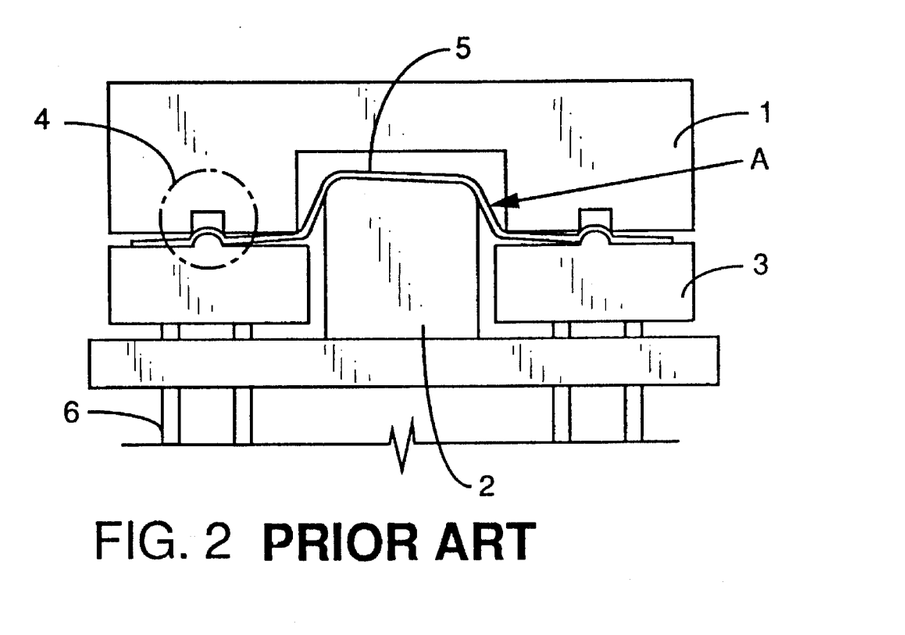
FIG. 2 is a sectional view showing a formation defect occurred during a stamping process.

Generally, the manufacturing process for the automotive body includes stamping, welding, coating and assembling. In the stamping process which is the first step of the manufacturing process, drawing, trimming and flanging are carried out by passing through 3 to 4 stamping dies. The formation defects such as fractures, buckling and the like which occur during the drawing step give influence to the later processes. As a result, the quality of the final products is deteriorated, and the productivity is lowered, thereby leading to the increase of the manufacturing cost. The drawing step of the stamping process, which plays the critical role in forming the automotive body will be described referring to the attached drawings, for the case where a single acting press is used. As shown in FIG. 1, a steel sheet 5 to be subjected to a formation is inserted into between a lower die 3 and an upper die 1 on which a draw bead 4 is installed. Then the upper die 1 is lowered, so that it should give a proper force to the steel sheet by the help of the reaction force of a cushion 6 which supports the lower die 3. At the same time, as shown in FIG. 2, the lower die 3 is lowered down to the depth of the panel to be formed. As the lower die 3 is lowered, the steel sheet 5 which is positioned between the upper die 1 and the lower die 3 passes through the draw bead 4 to be put into the upper die 1, so that the steel sheet should be formed in accordance with the shape of a punch 2, thereby completing the stamping process. However, as shown by the portion A of FIG. 2, fractures can occur on the wall of the formed panel during the drawing process. The occurrence of such fractures is very sensitively affected by the mechanical properties of the steel sheet, the design of the dies, and other stamping conditions.

The deformation which occurs to the steel sheet during the stamping process includes stretching and drawing deformations, and, in the former, the material is not permitted to be mobilized at the flange portion by the lock bead, while, in the latter, the mobilization of the material is accompanied in the flange portion. Meanwhile, the deformation mode in which the reduction of the thickness of the steel sheet occurs in connection with the fractures during the stamping process includes a bi-axial tensile deformation mode, and another deformation mode in which the deformation in one-direction is inhibited, and the deformation in the perpendicular direction exists. About 75–90% of the fractures which occur during the stamping process belong to a plane strain mode in which the deformation in one direction is zero. Therefore, in order to prevent fractures during the stamping process and to forecast the stamping formability, it is desirable to evaluate the stamping formability, i.e., the formability limit of the steel sheet under the plane strain mode.

There is a conventional method for evaluating the formability under the plane strain mode without considering the frictions between the die and the steel sheet. According to this conventional method, the steel sheet is formed into a tensile test piece having a shape such that the test specimen has multi-stepped widths. Then a tensile test is carried out to realize a plane strain mode, and then, the formability under the plane strain state is evaluated based on the tensile properties such as the elongation to the fracture. This conventional method cannot take into account the frictions occurring between the die and the steel sheet due to the surface condition of the steel sheet. Further, the plane strain state occurs locally on the central portion of the tensile test specimen, and a considerable time and caution are required in preparing the test specimen.

Figure 3:
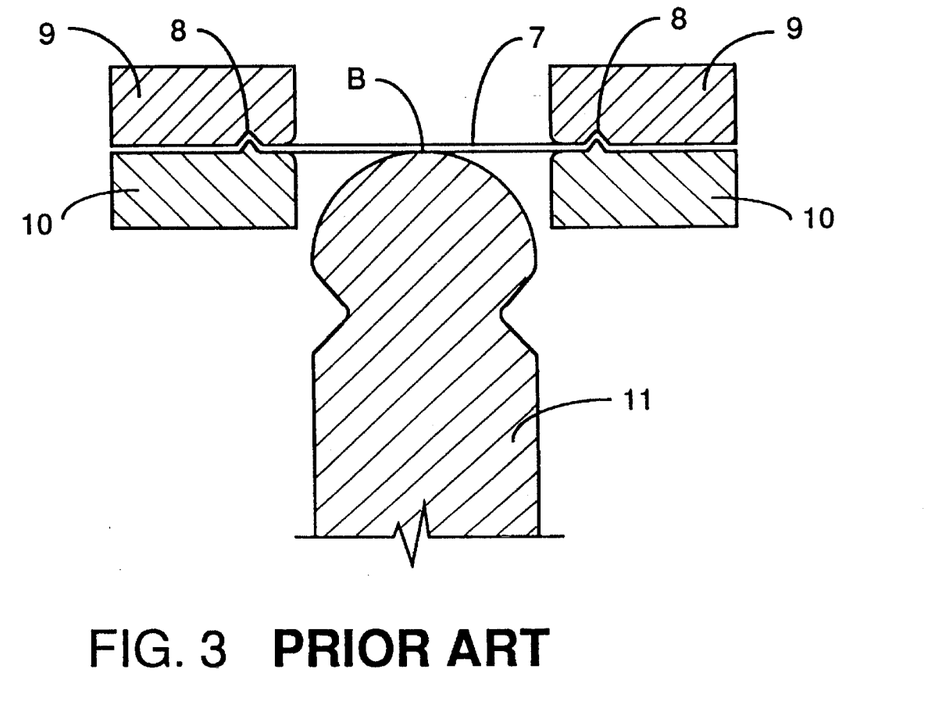
FIG. 3 is a sectional view of a conventional apparatus for evaluating the stretch formability.

Meanwhile, there is a conventional method for evaluating the stretch formability under the plane strain mode, with the contact between the die and the steel sheet being taken into account. That is, as shown in FIG. 3, a rectangular test specimen 7 which has a constant width and has a length longer than a lock bead 8 is inserted into between a lower die 10 and an upper die 9 on which the lock bead 8 is installed. Then the circumferential edge of the test specimen is strongly clamped by means of the lock bead 8, so that the material should not flow into the upper die 9. Then a dome shaped punch 11 having a diameter of 101.6 mm is elevated to apply the stretch formation force to the test specimen 7. Thus, the limit dome height LDH at the instant of the fracture of the test specimen 7 is recorded, thereby assessing the stretch formability under the plane strain mode.

Figure 4:
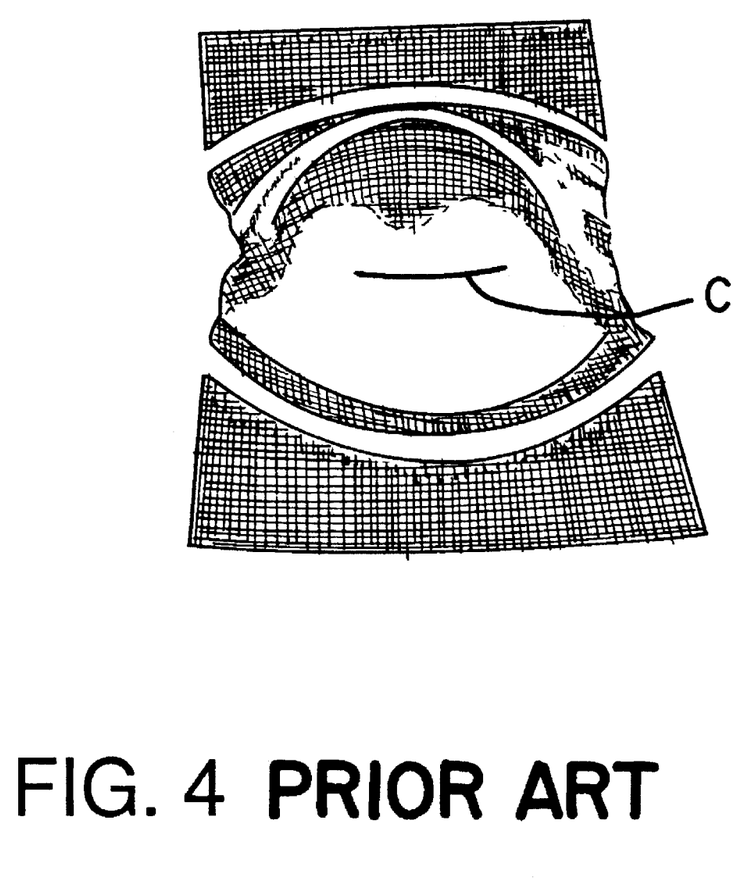
FIG. 4 is a photograph showing an etched test specimen formed by the conventional stretch formability test.

In this method, there is realized a geometrical restriction in which the test specimen 7 having a diameter larger than that of the dome shaped punch 11 and smaller than that of the lock bead 8 surrounds the peak portion B of the dome shaped punch 11. Further, there is obtained a plane strain state in which the deformation in the direction of the width of the test specimen 7 and around the fracture area C of the test specimen 7 is zero as shown in FIG. 4. According to this method, the plane strain state is realized only around the fracture area C, but the peak portion B of the punch does not represent the stretch formability under the plane strain mode in the stern standard of the bi-axial tensile state.

Further, in the case where there are differences in the surface roughness and other surface characteristics such as surface treatment among the test specimens, the width of the test specimens does not give constant values, and therefore, deviations are severe in the repeated tests for the height of the punch until a breaking occurs after the variation of the width. Further, in order to decide the width of the test specimen representing the plane strain mode, many rounds of repeated tests have to be carried out, and therefore, much time is consumed.

SUMMARY OF THE INVENTION

The present invention is intended to overcome the above described disadvantages of the conventional techniques.

Therefore it is the object of the present invention to provide an apparatus and a method for evaluating the plane strain stretch formability, in which the plane strain stretch formability for automotive steel sheet can be evaluated in advance for preventing fractures in stamping shops, and the evaluation for the plane strain stretch formability can be easily carried out in stamping shops.

In achieving the above object, the present invention is characterized in that: a rectangular test specimen having a certain width is inserted into a lower die and an upper die on which a lock bead is installed; the circumferential edge of the test specimen is tightly clamped by the lock bead so as for the material not to be mobilized into the upper die; then a semi-cylindrical punch having a length smaller than that of the rectangular test specimen is elevated to apply a stretch formation force on the test specimen; and then, the limit punch height at the instant of the breaking of the test specimen is recorded for evaluating the stretch formability under the plane strain mode, wherein the punch has a saddle-like semi-cylindrical shape.

BRIEF DESCRIPTION OF THE DRAWINGS

The above object and other advantages of the present invention will become more apparent by describing in detail the preferred embodiment of the present invention with reference to the attached drawings in which.

DESCRIPTION OF THE PREFERRED EMBODIMENT

Figure 5:
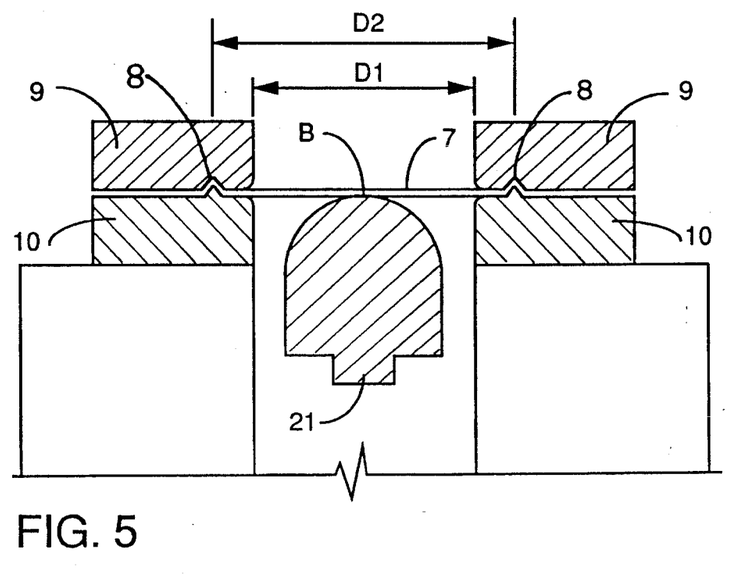
FIG. 5 is a sectional view of the plane strain stretch formability evaluating apparatus according to the present invention.

As shown in FIG. 5, the apparatus for evaluating the plane strain stretch formability according to the present invention includes: a lower die 10 and an upper die 9 on which lock bead 8 is installed. Within the upper and lower dies 9 and 10, there is installed a semi-cylindrical punch 21 which is movable up and down.

Figure 6:
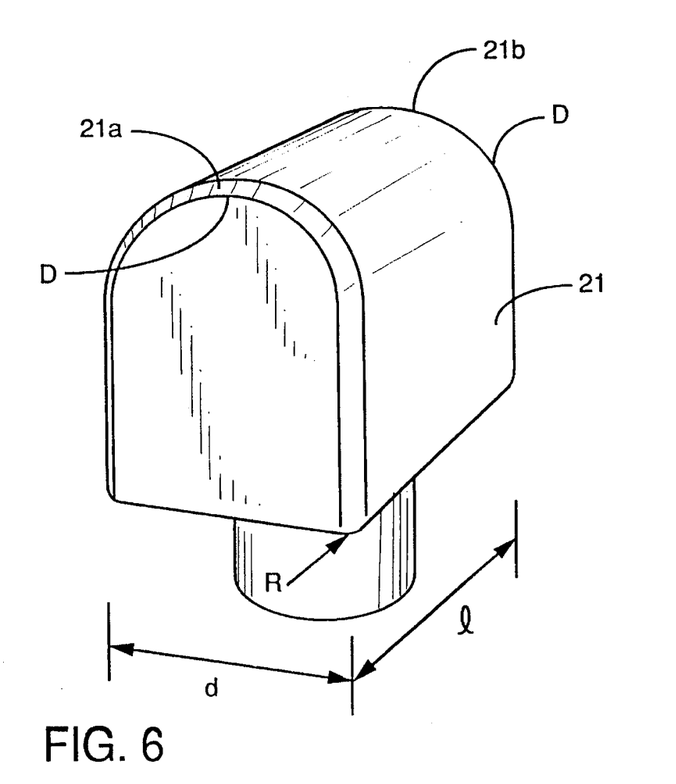
FIG. 6 is a perspective view of the semi-cylindrical punch of the plane strain stretch formability evaluating apparatus according to the present invention.

As shown in FIG. 6, the opposite edges 21a and 21b of the punch 21 are rounded with the same curvature, and the radius of curvature R should be desirably 5.0–9.0% of the length l of the punch 21. The reason is that, if the radius of curvature R is shorter than 5.0% of the punch length l, the deformation is concentrated on the rounded portion so as to cause a fracture on the test specimen, while, if the radius of curvature R is greater than 9.0% of the punch length l, the mobilization of the material is made in the direction of the width of the test specimen, i.e., in the lengthwise direction of the punch 21, whereby plane strain is not assured.

That is, the curvature of the edges of the punch 21 is designed such that the fracture probability due to the 90° bending should be eliminated, and that the flow of the material in the lengthwise direction of the punch is inhibited, whereby the plane strain is assured over the whole surface of the test specimen.

Meanwhile, as shown in FIGS. 5 and 6, the magnitudes of the length l and the diameter d of the semi-cylindrical punch 21 are designed such that the diagonal length $$\sqrt{d^2 + l^2}$$

should be smaller than the inside diameter D1 of the upper die 9, and the contact area between the punch 21 and the test specimen 7 should be as large as possible. The reason is that the magnitude of the friction between the punch 21 and the test specimen 7 affects the formability of the steel sheet. Further, the length of the rectangular test specimen 7 is made to be larger than the diameter D2 of the lock bead 8, and the width of the test specimen 7 is made to be smaller than the diameter D2 of the lock bead 8, so that, in accordance with the elevation of the punch 21, the test specimen should not be mobilized in the lengthwise direction, but the material of the test specimen 21 should be mobilized in the direction of the width, whereby the opposite edges 21a and 21b of the punch 21 are surrounded by the material.

Similarly to the case of the conventional dome shaped punch, the size and length of the punch according to the present invention are designed such that the influence of the mechanical properties of the test specimen to the stretch formability under the plane strain mode should be sufficiently considered, and that the characteristics of the frictions between the punch and the steel sheet should also be sufficiently considered. Because, if the contact area between the punch and the steel sheet is too small, the friction between the die and the steel sheet cannot be sufficiently evaluated. On the other hand, if the contact area is too large, the influence of the frictions is too much exaggerated relative to other mechanical properties of the steel sheet.

In the present invention, the desirable dimensions for the diameter d, the length l and the radius of curvature R of the rounded portion are 70 mm, 70 mm and 5 mm respectively.

Now the method for evaluating the plane strain stretch formability by using the plane strain stretch formability evaluating apparatus according to the present invention will be described.

As shown in FIG. 5, there is prepared a rectangular test specimen 7 which has a constant width in the rolling direction of the steel sheet, and which has a length larger than the diameter of the lock bead 8. This test specimen 7 is inserted into between the lower die 10 and the upper die 9 on which the lock bead 8 is installed. Then the circumferential edge of the test specimen 7 is strongly clamped by the lock bead 8, so that the material of the test specimen 7 should not be mobilized into the upper die 9.

Figure 8:
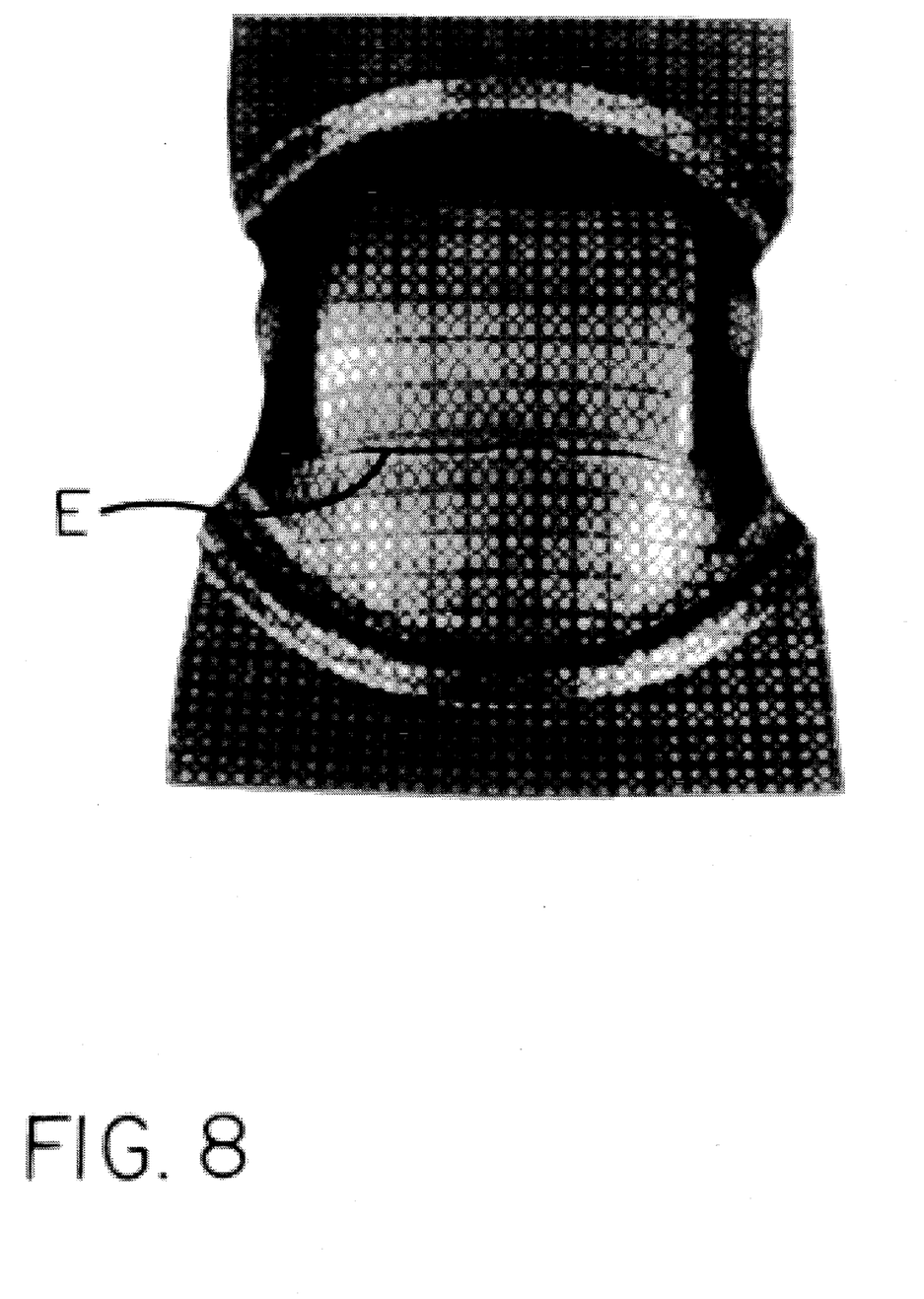
FIG. 8 is a photograph of an etched test specimen formed according to the present invention.

As shown in FIG. 6, by using the semi-cylindrical saddle-like punch 21, a stretch formation is carried out until the test specimen 7 breaks, and then, the plane strain stretch formability is evaluated based on the limit punch height LPH at the instant of the fracture of the test specimen. As the semi-cylindrical punch 21 is elevated, the test specimen 7 which has a width larger than that of the punch 21 is deformed in such a manner as to totally surround the punch 21. Meanwhile, if the lengthwise section of the punch is observed, the test specimen 7 is bent by about 90° at the opposite ends D of the punch 21, whereby the test specimen 7 is deformed into a U shaped form. As the punch 21 is elevated, the material flow is inhibited in the lengthwise direction of the punch 21 owing to the geometric restriction at the place where the test specimen is formed into a U shape by being bent by 90° at the opposite ends D of the punch 21. Therefore, the deformation of the test specimen 7 is concentrated on the arcuate portion of the semi-cylindrical punch 21. Thus the test specimen 7 maintains a plane strain state, and, as shown in FIG. 8, as the punch 21 is elevated, a fracture of the test specimen 7 occurs at the position E near the boundary of contact portion between the punch 21 and the test specimen 7. In the present invention, the superiority of the plane strain stretch formability, i.e., the stamping formability, is decided based on the limit punch height LPH at the instant of the fracture of the test specimen 7. That is, the higher the limit punch height to the fracture is, the more superior the formability of the material is. The lower the limit punch height is, the more inferior the formability of the material is. Meanwhile, in the case where the width of the test specimen is not larger than the length of the punch, the restriction of the material flow at the opposite ends of the semi-cylindrical punch is weakened, with the result that the material flow occurs, whereby a plane strain is not obtained. On the other hand, if the width of the*test specimen is too large, the restriction condition becomes too strong due to the bending deformation at the opposite ends D of the semi-cylindrical punch. Consequently, the fracture occurs too early at the opposite ends D due to the bending deformation, with the result that the stretch formability of the steel sheet cannot be known. Therefore, the width of the test specimen should be designed such that the plane strain should be assured on the whole surface of the test specimen.

In the present invention, the width of the test specimen is preferably designed such that it should be 1.78–1.82 time the length of the punch. The reason is that, if the width of the test specimen is less than 1.78 times the length of the punch, the material is mobilized in the direction of the width, whereby it is difficult to be assured of the plane strain. If it is more than 1.82 times the length of the punch, a bi-axial tensile state occurs, whereby it is impossible to be assured of the plane strain.

According to the present invention, the most desirable width of the test specimen is 126 mm, when the length of the punch is 70 mm.

According to the present invention, even if there are great differences in the surface characteristics due to the existence or absence of surface treatments or great differences in the mechanical properties such a anisotropic coefficient, still the width of the test specimen for obtaining the plane strain based on the geometric restriction conditions should be almost constant.

Now the actual examples of the present invention will be described.

<Example 1>

Test specimens having widths of 94 mm, 117 mm and 126 mm were prepared, and a stretch formability evaluating apparatus was used in which, for the semi-cylindrical punch, the radius of curvature R of the opposite edges 21a was 5 mm, the length Q was 70 mm, and the diameter d was 70 mm. Thus a plane strain stretch experiment was carried out, and then, the major and minor strains were measured. The major strain is illustrated in FIG. 7A, while the minor strain is illustrated in FIG. 7B.

The surface strain state of the test specimen was measured in the following manner. Circular grids having a size of 2.5 mm were etched on the surface of the test specimen before the formation, and an etching was carried out. Then a stretch formation was carried out to form the circular grid into an ellipse, and then, the major and minor strains for the longer side and shorter side were measured by using an optical grid measuring instrument.

Meanwhile, for the case-where the width of the test specimen was 126 mm, the photograph of the stretched and etched test specimen was observed. The test results are illustrated in FIG. 8.

Figure 7A:
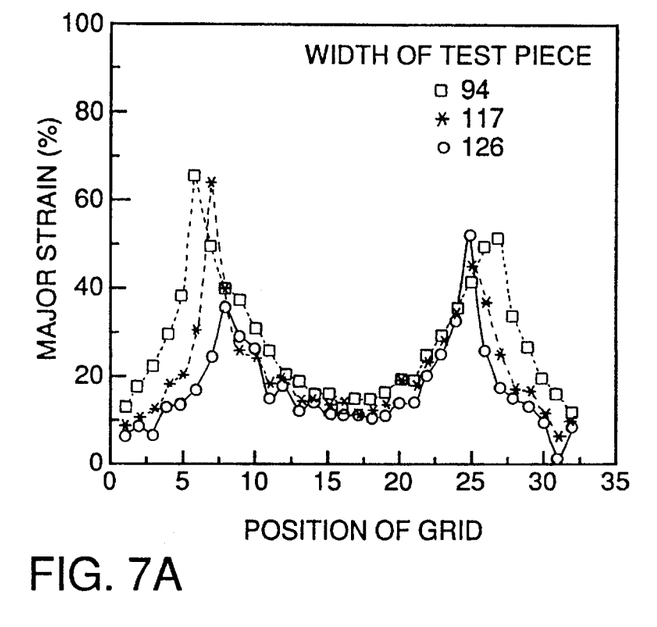
FIGS. 7A and 7B are graphical illustration showing the deformation rate distribution as against the width of the test specimen as a result of a plane strain test according to the present invention.
Figure 7B:
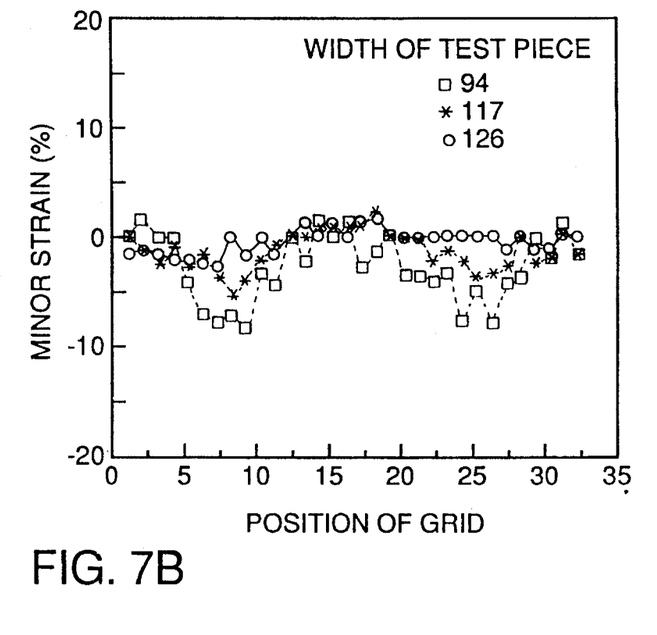

As shown in FIG. 7, in the case where the test specimen has a width of 126 mm according to the present invention, the minor strain occurred over the whole portion in the lengthwise direction in the rate of −3% 1%, thereby obtaining a plane strain having an minor strain of almost zero. In the case where a test specimen having a width departing from the size range of the present invention was used, the plane strain occurred only on a part of the whole portion.

FIG. 8 illustrates the form of the fracture of the test specimen in which the circular grid was uniformly etched, with the width of the test specimen being 126 mm, and with the evaluating apparatus of the present invention being used. The plane strain was as follows. That is, the deformed circles were such that the minor strain was almost zero over the whole surface of the test specimen including the portion of the fracture E.

Therefore, according to the present invention, if a proper width of the test specimen is used relative to the size of the punch, the plane strain stretch formability can be certainly evaluated.

<Example 2>

Figure 9A:
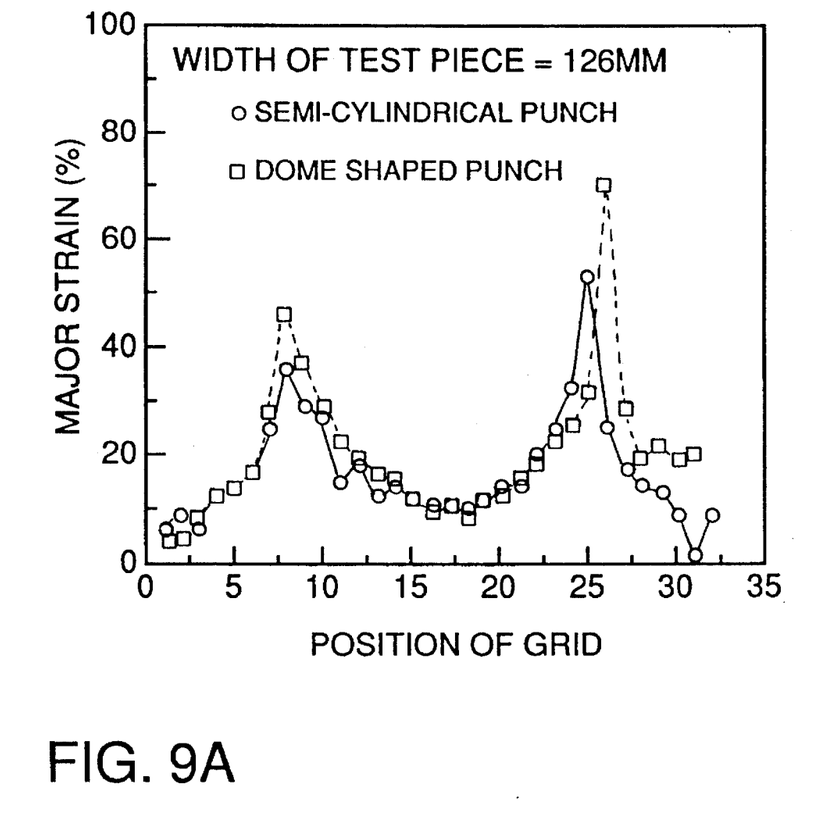
FIGS. 9A and 9B are graphical illustration comparatively showing the results of the conventional test and the test according to the present invention for the plane strain stretch formability.

The plane strain stretch experiments were carried out by using the conventional dome shaped punch (FIG. 3) and the semi-cylindrical punch of the present invention (FIG. 5). Then the major and minor strains were measured, and the major strain distribution is illustrated in FIG. 9A, while the minor strains are illustrated in FIG. 9B.

Figure 9B:
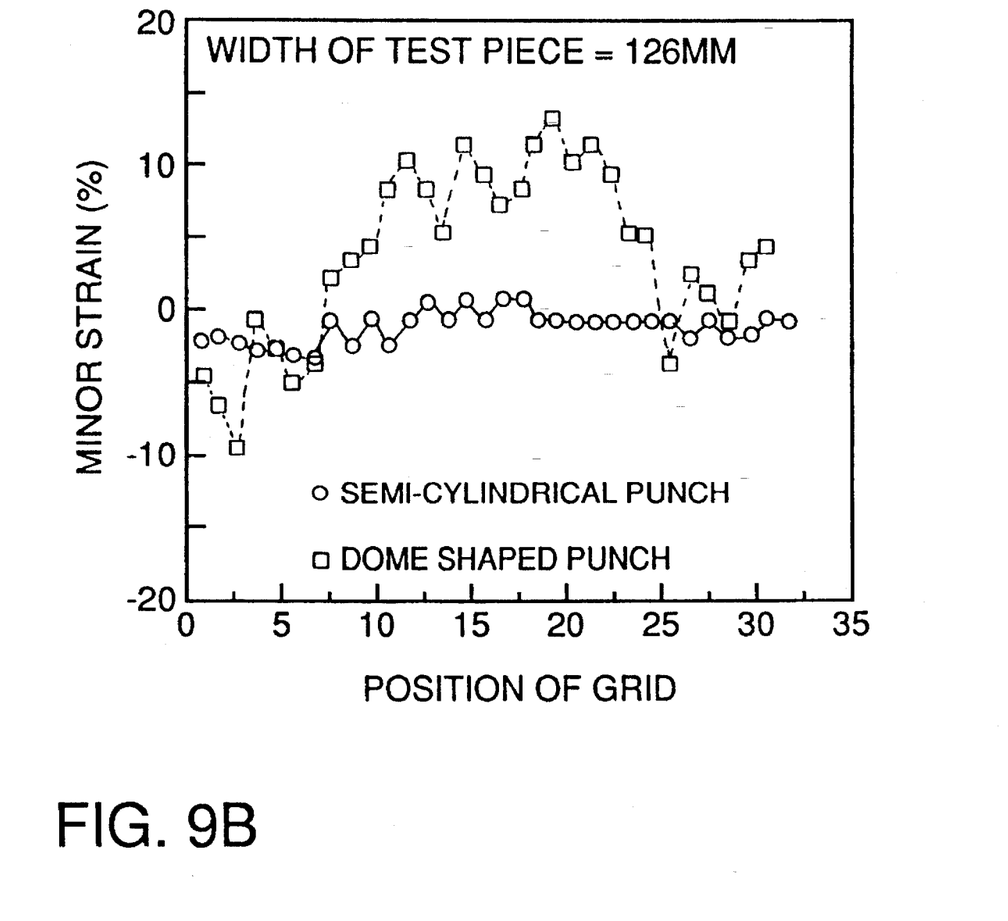

As shown in FIG. 9B, in the case of the conventional dome shaped punch, a plane strain was obtained in which the minor strain was zero only near the fractured portion. On the other hand, in the case of the semi-cylindrical punch according to the present invention, a plane strain was obtained in which the minor strain is zero over the whole surface of the test specimen.

<Example 3>

The plane strain stretch formability tests were carried out for the typical steel sheets for automotive bodies, and the limit punch height and the Erichsen values are shown in Table 1 below.

TABLE 1

| steel sheet | yield strength kgf/mm² | tensile strength kgf/mm² | elongation % | erichsen vale mm | LPH of invention mm |
| --- | --- | --- | --- | --- | --- |
| CQ | <21 | >28 | >42 | >9.4 | >30.9 |
| DQ | <20 | >28 | >43 | >10.0 | >31.5 |
| DDQ | <18 | >28 | >45 | >10.4 | >32.6 |
| EDDQ | <16 | >28 | >48 | >10.9 | >34.0 |

As shown in Table 1 above, the Erichsen value which has been widely used in evaluating the stretch formability of the steel sheets conventionally do not show much differences. On the other hand, the limit punch height for the fracture in the plane strain stretch formability test according to the present invention shows much differences for the different steel sheets. The elongation of the material is raised in the order of CQ<DQ<DDQ<EDDQ, and the limit punch heights are also same, thereby making it possible to distinguish the steel sheets.

According to the present invention as described above, there are provided an apparatus and a method for evaluating fracture limit and the stretch formability under the plane strain mode which occupies the most parts of the fractures occurring in the stamping process of the automotive steel sheets. That is, a semi-cylindrical punch is used, and the stretch formability is evaluated by using a test specimen having a width larger than the length of the punch. Thus the plane strain stretch formability, i.e., the stamping formability is evaluated based on the fracture limit punch height in a simple manner, so that fractures in the actual stamping process can be predicted.

What is claimed is:

1. An apparatus for evaluating a plane strain stretch formability of thin steel sheet material, comprising:

a mating lower die and an upper die having a central opening therein and having complementary grooved and raised surface areas defining a lock bead circumscribing the central opening for clamping a test specimen of said sheet material therebetween;

a punch, movable within the central opening of the dies, said punch having a saddle-like, semi-cylindrical shape for engaging said test specimen, said punch having a length Z defined as a distance between opposed semi-cylindrical ends of said punch and wherein said test specimen is rectangular in shape having a width which is greater than the length of said punch;

whereby, in use, said punch is moved to apply a stretch force on said test specimen, wherein said punch moves a distance to stretch and subsequently fracture said test specimen under a plane strain mode and the stretch formability of said sheet material is evaluated based on a fracture limit punch height defined by the distance travelled by said punch from first contacting said test specimen until fracture thereof.

2. A method for evaluating a plane strain stretch formability of a thin sheet material comprising the steps of:

providing a rectangularly configured test specimen of said thin sheet material;

providing a mating lower die and an upper die having a central opening therein and having complementary grooved and raised surface areas defining a lock bead means around the central opening;

providing a punch, movable within the central opening of the dies, said punch having a saddle-like, semi-cylindrical shape for engaging said test specimen, said punch having a length Z defined as a distance between opposed semi-cylindrical ends of said punch and wherein said rectangular test specimen has a width 1.78 to 1.82 times the length Z of said punch;

inserting said test specimen between said lower and upper dies;

closing said dies and clamping said test specimen with said lock bead means;

moving said punch to engage said test specimen to apply a stretch force on said test specimen to stretch and subsequently fracture said test specimen under a plane strain mode; and measuring the distance traveled by the punch from first engagement with the test specimen until fracture thereof to define a fracture limit punch height for said thin sheet material.

3. The apparatus as claimed in claim 1, wherein the edges of said punch are rounded with a certain curvature.

4. The apparatus as claimed in claim 3, wherein the radius of curvature for the rounded edges portion is equivalent to 5–9% of the length l of said punch.

5. The apparatus as claimed in claim 3, wherein said punch has a length l of 70 mm, a diameter of 70 mm and a radius of curvature R of 5 mm.

6. The method as claimed in claim 2, wherein the length l of said punch is 70 mm, and the width of said test specimen is 126 mm.

7. An apparatus for evaluating a plane strain stretch formability of thin steel sheet material, comprising:

a mating lower die and an upper die having a central opening therein and having complementary grooved and raised surface areas defining a lock bead circumscribing the central opening for clamping a test specimen of said sheet material therebetween;

a punch, movable within the central opening of the dies, said punch having a saddle-like, semi-cylindrical shape for engaging said test specimen, said punch having a length l defined as a distance between opposed semi-cylindrical ends of said punch and having rounded edges of a certain curvature and wherein said test specimen is rectangular in shape having a width which is greater than the length of said punch;

whereby, in use, said punch is moved to apply a stretch force on said test specimen, wherein said punch moves a distance to stretch and subsequently fracture said test specimen under a plane strain mode and the stretch formability of said sheet material is evaluated based on a fracture limit punch height defined by the distance travelled by said punch from first contacting said test specimen until fracture thereof.

8. An apparatus for evaluating a plane strain stretch formability of thin steel sheet material, comprising:

a mating lower die and an upper die having a central opening therein and having complementary grooved and raised surface areas defining a lock bead circumscribing the central opening for clamping a test specimen of said sheet material therebetween;

a punch, movable within the central opening of the dies, said punch having a saddle-like, semi-cylindrical shape for engaging said test specimen, said punch having a length defined as a distance between opposed semi-cylindrical ends of said punch and having l rounded edges at said ends, said rounded edges having a radius of curvature equivalent to 5–9% of the length e, and wherein said test specimen is rectangular in shape having a width which is greater than the length of said punch;

whereby, in use, said punch is moved to apply a stretch force on said test specimen, wherein said punch moves a distance to stretch and subsequently fracture said test specimen under a plane strain mode and the stretch formability of said sheet material is evaluated based on a fracture limit punch height defined by the distance travelled by said punch from first contacting said test specimen until fracture thereof.

9. An apparatus for evaluating a plane strain stretch formability of thin steel sheet material, comprising:

a mating lower die and an upper die having a central opening therein and having complementary grooved and raised surface areas defining a lock bead circumscribing the central opening for clamping a test specimen of said sheet material therebetween;

a punch, movable within the central opening of the dies, said punch having a saddle-like, semi-cylindrical shape for engaging said test specimen, said punch having a diameter of 70 mm and a length l of 70 mm defined as a distance between opposed semi-cylindrical ends of said punch and having rounded edges at said ends, said rounded edges having a radius of curvature R of 5 mm, and wherein said test specimen is rectangular in shape having a width which is greater than the length l of said punch;

whereby, in use, said punch is moved to apply a stretch force on said test specimen, wherein said punch moves a distance to stretch and subsequently fracture said test specimen under a plane strain mode and the stretch formability of said sheet material is evaluated based on a fracture limit punch height defined by the distance travelled by said punch from first contacting said test specimen until fracture thereof.

10. A method for evaluating a plane strain stretch formability of a thin sheet material comprising the steps of:

providing a rectangularly configured test specimen of said thin sheet material;

providing a mating lower die and an upper die having a central opening therein and having complementary grooved and raised surface areas defining a lock bead means around the central opening;

providing a punch, movable within the central opening of the dies, said punch having a saddle-like, semi-cylindrical shape for engaging said test specimen, said punch having a length l of 70 mm defined as a distance between opposed semi-cylindrical ends of said punch and wherein said rectangular test specimen has a width of 126 mm;

inserting said test specimen between said lower and upper dies;

closing said dies and clamping said test specimen with said lock bead means;

moving said punch to engage said test specimen to apply a stretch force on said test specimen to stretch and subsequently fracture said test specimen under a plane strain mode; and measuring the distance travelled by the punch from first engagement with the test specimen until fracture thereof to define a fracture limit punch height for said thin sheet material.

* * * * *

UNITED STATES PATENT AND TRADEMARK OFFICE
CERTIFICATE OF CORRECTION

PATENT NO. : 5,507,189
DATED : April 16, 1996
INVENTOR(S) : Young S. Kim, Jeong C. Kim, Won J. Choi, Rae W. Chang, Ki S. Kim and Moon H. Yu It is certified that error appears in the above-indentified patent and that said Letters Patent is hereby corrected as shown below:

Title page, item '[56] References Cited, U.S. PATENT DOCUMENTS', "2,645,937 7/1953 Kalmusky et al. ... 73/838" should read --2,645,937 7/1953 Skalmusky et al. ... 73/838--.

Column 1 Line 59 "one-direction" should read --one direction--.

Column 3 Line 33 "illustration" should read --illustrations--.

Column 3 Line 39 "illustration" should read --illustrations--.

Column 5 Line 20 "the*test" should read --the test--.

Column 5 Line 30 "time" should read --times--.

Column 5 Line 57 "Q" should read --1--.

Column 6 Line 3 "case-where" should read --case where--.

Column 6 Line 10 "-3% 1%," should read -- -3% - 1%,--.

Claim 1 Line 27 Column 7 "Z" should read --1--.

Claim 2 Line 51 Column 7 "Z" should read --1--.

UNITED STATES PATENT AND TRADEMARK OFFICE
CERTIFICATE OF CORRECTION

PATENT NO. : 5,507,189
DATED : April 16, 1996
INVENTOR(S) : Young S. Kim, Jeong C. Kim, Won J. Choi, Rae W. Chang, Ki S. Kim and Moon H. Yu It is certified that error appears in the above-indentified patent and that said Letters Patent is hereby corrected as shown below:

Claim 2 Line 54 Column 7 "Z" should read --1--.

Claim 4 Line 4 Column 8 "edges portion" should read --edges--.

Claim 5 Line 6 Column 8 "3," should read --4,--.

Claim 8 Line 46 Column 8 before "defined" insert --1--.

Claim 8 Line 47 Column 8 "having 1 rounded" should read --having rounded--.

Claim 8 Line 49 Column 8 "e," should read --1,--.

Signed and Sealed this

Seventeenth Day of September, 1996

Attest:

BRUCE LEHMAN

Attesting Officer    Commissioner of Patents and Trademarks